(12) United States Patent
Hassan et al.

(10) Patent No.: US 8,759,570 B2
(45) Date of Patent: Jun. 24, 2014

(54) HIGH SHEAR SYSTEM AND PROCESS FOR THE PRODUCTION OF HALOGENATED AND/OR SULFONATED PARAFFINS

(75) Inventors: Abbas Hassan, Houston, TX (US); Aziz Hassan, Houston, TX (US); Krishnan Viswanathan, Houston, TX (US); Greg G. Borsinger, Chatam, NJ (US); Rayford G. Anthony, Houston, TX (US)

(73) Assignee: H R D Corporation, Houston, TX (US)

( * ) Notice: Subject to any disclaimer, the term of this patent is extended or adjusted under 35 U.S.C. 154(b) by 635 days.

(21) Appl. No.: 13/038,906
(22) Filed: Mar. 2, 2011
(65) Prior Publication Data
US 2011/0269989 A1    Nov. 3, 2011

Related U.S. Application Data (60) Provisional application No. 61/310,885, filed on Mar. 5, 2010.

(51) Int. Cl.
*C07C 309/00*    (2006.01)
(52) U.S. Cl.
USPC .......................................................... 562/115
(58) Field of Classification Search
USPC ................................................. 562/113, 115
See application file for complete search history.

(56) References Cited

U.S. PATENT DOCUMENTS

| | | | |
|---|---|---|---|
| 3,438,742 A | 4/1969 | Grunewald et al. | |
| 3,887,167 A | 6/1975 | Irwin | |
| 4,100,212 A * | 7/1978 | Di Fiore et al. ............... | 570/252 |
| 5,538,191 A | 7/1996 | Holl | |
| 5,877,350 A | 3/1999 | Langer et al. | |
| 6,368,366 B1 | 4/2002 | Langer et al. | |
| 6,368,367 B1 | 4/2002 | Langer et al. | |
| 6,383,237 B1 | 5/2002 | Langer et al. | |
| 6,530,964 B2 | 3/2003 | Langer et al. | |
| 6,742,774 B2 | 6/2004 | Holl | |
| 6,868,366 B1 | 3/2005 | Eisenzopf | |
| 2003/0043690 A1 | 3/2003 | Holl | |
| 2004/0052158 A1 | 3/2004 | Holl | |
| 2005/0033069 A1 | 2/2005 | Holl et al. | |
| 2009/0005609 A1 | 1/2009 | Hassan et al. | |
| 2009/0005619 A1 | 1/2009 | Hassan et al. | |
| 2010/0004419 A1 | 1/2010 | Hassan et al. | |

FOREIGN PATENT DOCUMENTS

| | | |
|---|---|---|
| CN | 100450855 | 1/2009 |
| JP | 2009500165 | 1/2009 |
| JP | 2009132675 | 6/2009 |
| WO | WO 0015607 A1 * | 3/2000 |
| WO | 02064708 | 8/2002 |
| WO | 20090122438 | 10/2009 |

OTHER PUBLICATIONS

F.A. Carey, Organic Chemistry, 6th Ed. (2006), Ch. 23.*
Chattopadhyay et al., "Understanding Mechanical Energy Driven Nonequilibrium Processing: Some Results, Eleventh Internatinal Conference on Rapidly Quenched and Metastable Materials," A Material Science and Engineering, vol. 375-377, dated Jul. 15, 2004, pp. 72-77 (9 pgs.).
IKA-Rotor-Stator Generators—2003 Processing Catalog (38 pgs.).
Gogate, et al. "Cavitation: A technology on the horizon," Current Science 91, No. 1, Jul. 2006, pp. 35-46 (12 pgs.).
Office Action dated Jun. 25, 2009 for U.S. Appl. No. 12/142,447 (10 pgs.).
Office Action dated Jan. 7, 2010 for U.S. Appl. No. 12/142,447 (6 pgs.).
Office Action dated May 13, 2010 for U.S. Appl. No. 12/142,447 (5 pgs.).
Office Action dated Feb. 4, 2010 for U.S. Appl. No. 12/492,721 (5 pgs.).
Office Action dated Feb. 18, 2010 for U.S. Appl. No. 12/635,433 (6 pgs.).
Office Action dated Feb. 18, 2010 for U.S. Appl. No. 12/635,454 (6 pgs.).
Office Action dated May 14, 2010 for U.S. Appl. No. 12/137,441 (15 pgs.).
Office Action dated Feb. 19, 2010 for U.S. Appl. No. 12/144,459 (10 pgs.).
Office Action dated Sep. 2, 2009 for U.S. Appl. No. 12/142,433 (11 pgs.).
Office Action dated Jan. 29, 2010 for U.S. Appl. No. 12/142,433 (8 pgs.).
Office Action dated May 24, 2011 for U.S. Appl. No. 12/142,433 (10 pgs.).
Office Action dated Apr. 30, 2010 for U.S. Appl. No. 12/141,191 (12 pgs.).
Office Action dated Oct. 27, 2009 for U.S. Appl. No. 12/142,120 (15 pgs.).
Office Action dated May 5, 2010 for U.S. Appl. No. 12/571,537 (12 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
Office Action dated Jun. 2, 2011 for U.S. Appl. No. 12/427,286 (12 pgs.).
Office Action dated Jun. 3, 2011 for U.S. Appl. No. 12/568,280 (16 pgs.).
IKA, "Introduction to IKA's Three Stage Dispax Reactor," Retrieved from <http://www.ikausa.com/pdfs/process/dr%202000-Homogenizing-Dispersing-Suspending-Emulsifying.pdf> on Aug. 22, 2012 (12 pgs.).

(Continued)

*Primary Examiner* — Porfirio Nazario Gonzalez
*Assistant Examiner* — Kofi Adzamli
(74) *Attorney, Agent, or Firm* — Timothy S. Westby; Porter Hedges, LLP (57) ABSTRACT

A method for halogenating, sulfonating, or sulfo-halogenating a feed comprising paraffin, by subjecting a mixture comprising the feed and a reagent selected from the group consisting of sulfonating agents, halogenating agents, and combinations thereof to a shear rate of at least 20,000 s$^{-1}$ to produce a high-shear treated product; cooling the high shear-treated product by heat exchange with a heat transfer medium, to produce a cooled product; and separating the high shear-treated product into an offgas and a liquid product comprising at least one selected from the group consisting of sulfonated paraffins, halogenated paraffins, and sulfo-halogenated paraffins. A high shear system for the production of halogenated, sulfonated, or sulfo-halogenated paraffin is also provided.

20 Claims, 2 Drawing Sheets

(56) References Cited

OTHER PUBLICATIONS

IKA-DRS Reactors website http://www.ikausa.com/dr.him, on Sep. 8, 2010 (2 pgs.).

International Report on Patentability dated Sep. 11, 2012 for corresponding International Application No. PCT/US2011/026789 (4 pgs.).

Search Report and Written Opinion dated Nov. 28, 2011 for corresponding International Application No. PCT/US2011/026789 (8 pgs.).

European Search Report dated Jun. 28, 2013 for corresponding EPO Application No. 11751253.3-1352 (6 pgs.).

Chattopadhyay et al., "Understanding Mechanical Energy Driven Nonequilibrium Processing: Some Results Eleventh Internatinal Conference on Rapidly Quenched and Metastable Materials," A Material Science and Engineering, vol. 375-377, dated Jul. 15, 2004, pp. 72-77 (9 pgs.).

* cited by examiner

HIGH SHEAR SYSTEM AND PROCESS FOR THE PRODUCTION OF HALOGENATED AND/OR SULFONATED PARAFFINS

CROSS-REFERENCE TO RELATED APPLICATIONS

This application claims the benefit under 35 U.S.C. §119(e) of U.S. Provisional Patent Application No. 61/310,885, entitled "High Shear System and Process for The Production of Halogenated and/or Sulfonated Paraffins" filed Mar. 5, 2010, the disclosure of which is hereby incorporated herein by reference in its entirety.

STATEMENT REGARDING FEDERALLY SPONSORED RESEARCH OR DEVELOPMENT

Not Applicable.

BACKGROUND

1. Technical Field

The present disclosure relates generally to the halogenation and/or sulfonation of paraffins and, more particularly, to apparatus and methods for producing halogenated and/or sulfonated paraffins utilizing high shear. More specifically, this disclosure pertains to the reduction of mass transfer limitations for halogenating, sulfonating, or sulfo-halogenating a feed comprising paraffins.

2. Background of the Invention

Chlorinated paraffins (CPs), which were introduced in the 1930s, are a complex mixture of polychlorinated n-alkanes. The chlorination degree of CPs generally varies between about 30 and 70%. CPs are subdivided according to their carbon chain length into short chain CPs (SCCPs, C10-13), medium chain CPs (MCCPs, C14-17) and long chain CPs (LCCPs, C>17). Over 200 CP formulations are currently in use for a wide range of industrial applications, including application as flame retardants and plasticizers and as additives in metal working fluids, in sealants, paints and coatings.

The largest application for chlorinated paraffins is as a plasticizer. In flexible PVC, chlorinated paraffins are generally utilized in conjunction with primary plasticizers, such as various phthalates. The use of chlorinated paraffins in PVC imparts a number of benefits such as the enhancement of flame retardant properties. Such properties are of particular value in the production of PVC flooring and cables.

Chlorinated paraffins are also used as plasticizers in paint, sealants and adhesives, where the main advantages thereof over available alternatives are the relative inertness of CPs and the enhancement of flame retardant properties provided thereby. Chlorinated paraffins of higher chlorine content grades are utilized as flame retardants in a wide range of rubbers and polymer systems and may be preferable to phosphate and/or bromine-based additives.

Another major outlet for chlorinated paraffins is in the formulation of metal working lubricants. Chlorinated paraffins have long been recognized as one of the most effective extreme pressure additives for lubricants that find application in a gamut of machining and engineering operations.

U.S. Pat. No. 4,100,212 describes conventional processes for chlorination of linear paraffins. As noted therein, it is desirable to achieve a rapid and efficient homogenization of the liquid and gaseous reactants and it is often difficult to achieve complete conversion of reagent chlorine even with utilization of relatively long contact times.

Accordingly, there is a need in the industry for improved systems and methods for producing halogenated, sulfonated, or sulfo-halogenated paraffins, whereby costs may be reduced via operation at lower temperature and/or pressure, product yield may be increased, reaction time may be decreased, and/or capital and/or operating costs may be reduced. Desirably, conversion of reagent (e.g. chlorine or other halogen gas) is substantially complete and/or time of contact of feed material to be treated with treatment aid (e.g. reagent) is decreased via the method relative to conventional systems and methods.

SUMMARY

Herein disclosed is a method for halogenating, sulfonating, or sulfo-halogenating a feed comprising paraffin, the method comprising: subjecting a mixture comprising the feed and a reagent selected from the group consisting of sulfonating agents, halogenating agents, and combinations thereof to a shear rate of at least $20,000\ s^{-1}$ to produce a high-shear treated product; cooling the high shear-treated product by heat exchange with a heat transfer medium, to produce a cooled product; and separating the high shear-treated product into an offgas and a liquid product comprising at least one selected from the group consisting of sulfonated paraffins, halogenated paraffins, and sulfo-halogenated paraffins. In embodiments, subjecting the mixture to a shear rate of at least 20,000 $s^{-1}$ further comprises introducing the mixture into a high shear device comprising at least one rotor and at least one complementarily-shaped stator, and operating at a rotor tip speed of at least 5 m/s. In embodiments, cooling the high shear-treated stream further comprises holding the high shear-treated stream in a residence time vessel configured with a heat exchanger. The method can further comprise preheating the feed. In embodiments, the feed comprises linear paraffin. In embodiments, the feed comprises paraffin wax. In embodiments, the feed comprises liquid n-paraffin. In embodiments, the feed comprises at least one selected from the group consisting of paraffin oils, paraffin waxes, and polyethylene waxes. The halogenating agent can comprise a gas selected from the group consisting of halogens. In embodiments, subjecting the mixture to a shear rate of at least 20,000 $s^{-1}$ produces a dispersion comprising gas bubbles having an average diameter of less than about 5 μm. In embodiments, subjecting the mixture to a shear rate of at least 20,000 $s^{-1}$ produces a dispersion comprising gas bubbles having an average diameter of less than about 1 μm. The reagent can be selected from the group consisting of sulfuric acid and oleum. The high shear treated stream can have a temperature in the range of from about 25° C. to about 150° C. The method can further comprise recycling at least a portion of the liquid product and forming additional high shear-treated product therefrom. The method can further comprise maintaining a desired temperature of the high shear-treated stream by adjusting at least one selected from the group consisting of the amount of reagent, the portion of the liquid product recycled, the temperature of the heat transfer medium, and the flow rate of the heat transfer medium. In embodiments, the reagent comprises chlorine gas, the offgas comprises hydrogen chloride gas, and the method further comprises contacting the offgas with water to produce aqueous hydrogen chloride. The aqueous hydrogen chloride can comprise from about 30 wt % to about 70 wt % hydrogen chloride. In embodiments, at least one selected from the group consisting of the high shear treated product, the cooled product, and the liquid product comprises a stabilizer. The stabilizer can be selected from the group consisting of organo tin compounds, and mercaptides, carboxylates, sulfides and maleates of at least one Group II metal and at least one Group 14 metal. In embodiments, the halogenation, sulfonation, or sulfo-halogenation is conducted in the presence of a catalyst. In embodiments, the catalyst is a homogeneous chlorination catalyst selected from the group consisting of iodine, phosphorus, sulfur, antimony chloride, iron chloride, zinc chloride, and combinations thereof. The method can further comprise separating from the cooled product at least one selected from the group consisting of short chain products comprising primarily C10-C13 compounds, medium chain products comprising primarily from C14-C17 compounds, and long chain length products comprising primarily from C18-C30 compounds.

Also disclosed herein is a system for the production of halogenated, sulfonated, or sulfo-halogenated paraffin, the system comprising: a high shear device operable to subject a mixture of reagent and feed comprising paraffin to a shear rate of at least 20,000 $s^{-1}$; a residence time vessel configured with a heat exchanger; the residence time vessel fluidly connected to an outlet of the high shear device; and a phase separator configured for separation of a gas from a liquid product, the separator fluidly connected with an outlet of the residence time vessel. In embodiments, the high shear device is operable to subject the mixture of reagent and feed comprising paraffin to a shear rate of at least 30,000 $s^{-1}$. In embodiments, the reagent is gaseous and the high shear device is operable to produce a dispersion of the gaseous reagent in the feed. In embodiments, the dispersion comprises gas bubbles having an average diameter of less than about 5 μm. In embodiments, the dispersion comprises gas bubbles having an average diameter of less than about 1 μm. In embodiments, the high shear device comprises at least one rotor and is operable to provide a tip speed of the at least one rotor of at least about 5 m/s. In embodiments, the high shear device is operable to provide a tip speed of the at least one rotor of at least about 22 m/s. In embodiments, the high shear device produces a localized pressure of at least about 1000 MPa at the tip of the at least one rotor during operation. The system can further comprise a preheater upstream of the high shear device and configured to heat the feed to a desired temperature prior to introduction into the high shear device. In embodiments, the feed is a paraffin wax that is solid at room temperature. The system can further comprise a scrubber downstream of the phase separator and configured to scrub at least one component from the gas via contact with a scrubbing liquid. The scrubbing liquid can comprise water and the at least one component can comprise hydrochloric acid. The system can further comprise a recycle line fluidly connecting a liquid product outlet of the phase separator with the high shear device whereby at least a portion of the liquid product may be recycled to the high shear device. In embodiments, the high shear device comprises at least two generators, wherein each generator comprises a rotor and a complementarily-shaped stator. In embodiments, the high shear device comprises at least three generators.

These and other embodiments, features, and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

NOTATION AND NOMENCLATURE

As used herein, the term 'dispersion' refers to a liquefied mixture that contains at least two distinguishable substances (or 'phases'). As used herein, a 'dispersion' comprises a 'continuous' phase (or 'matrix'), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. As used herein, the term "dispersion" encompasses continuous liquid phases throughout which gas bubbles are distributed, continuous liquid phases throughout which solid particles are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles is distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination. A dispersion may comprise, for example, bubbles of gas (e.g. halogenation/sulfonation agent) in a liquid (e.g. in feedstock comprising paraffin) and/or droplets of one fluid in a phase with which it is immiscible.

Although paraffin, or paraffin hydrocarbon, is the technical name for an alkane in general, in most cases as used herein it specifically refers to a linear or normal alkane, whereas branched, or isoalkanes are referred to as isoparaffins. In chemistry, paraffin is the common name for the alkane hydrocarbons with the general formula $C_nH_{2n+2}$. Paraffin wax refers to paraffins that are solid at room temperature (generally paraffins for which $20 \leq n \leq 40$).

Use of the phrase, 'all or a portion of' is used herein to mean 'all or a percentage of the whole' or 'all or some components of.'

DETAILED DESCRIPTION

Overview.

In halogenation (e.g. chlorination) of paraffins, it is generally understood that a large contact area between the liquid and gas phases will improve the homogeneity of the product and provide a high mass transfer coefficient. The system and method disclosed herein employ an external high shear mechanical device to provide rapid contact and mixing of chemical ingredients in a controlled environment within the reactor/mixer device, thus reducing mass transfer limitations on the reaction and increasing the overall reaction rate.

Chemical reactions involving liquids, gases and solids rely on the laws of kinetics that involve time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there may be the additional rate limiting factor of having the reaction products migrate away/removed from the surface of the catalyst thus enabling the catalyst to catalyze further reactants.

In conventional reactors, contact time for the reactants and/or catalyst is often controlled by mixing which provides contact between two or more reactants involved in a chemical reaction. A reactor assembly that comprises an external high shear mixer as disclosed herein makes possible decreased mass transfer limitations and thereby allows the reaction to more closely approach kinetic limitations. When reaction rates are accelerated, residence times may be decreased, thereby increasing obtainable throughput. Alternatively, where the current yield is acceptable, decreasing the required residence time may allow for the use of lower temperatures and/or pressures than conventional processes.

Although at times described with respect to chlorination, it is to be understood that the disclosed system and method are equally applicable to other halogenations such as bromination, to sulfonation, and to sulfo-halogenation.

High Shear System.

Figure 1:
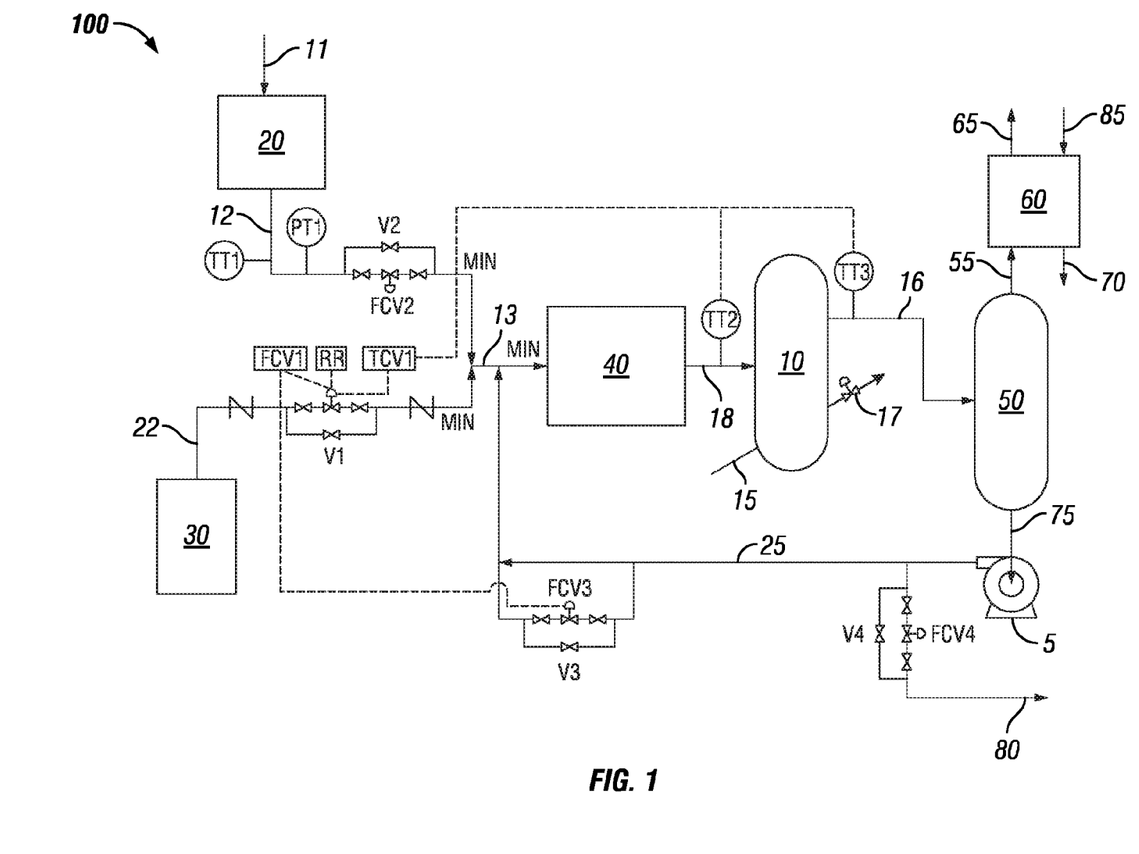
FIG. 1 is a schematic of a high shear system for production of sulfonated and/or halogenated paraffin according to an embodiment of the present disclosure.

Herein disclosed is a high shear system for the production of halogenated and/or sulfonated paraffins. FIG. 1 is a schematic of a system 100, according to an embodiment of this disclosure. The high shear system comprises a high shear mixing device, a residence time vessel (sometimes referred to herein as RTV) and a gas/liquid separator. In embodiments, the system further comprises a preheater, a feed gas source, a pump, a scrubber, or any combination thereof. In the embodiment of FIG. 1, system 100 comprises high shear mixing device (also referred to herein as high shear device or HSD) 40, residence time vessel 10, gas/liquids separator 50, pump 5, scrubber 60, reagent source 30 and preheater 20. As will be discussed in more detail hereinbelow, HSD 40 is positioned upstream of and fluidly connected with residence time vessel 10 and is configured for subjecting the contents therein to high shear, providing a high shear treated stream to residence time vessel 10. Residence time vessel 10 is positioned upstream of and is fluidly connected with gas/liquid separator 50. One or more pumps 5 may be positioned within system 100 to provide controlled flow throughout system 100 and/or to provide feed to HSD 40 at a desired pressure. A pump 5 may be positioned, for example on a product line 75 fluidly connected with gas/liquid separator 50 and configured for removal of liquid product therefrom. In embodiments, a preheater 20 is positioned upstream of HSD 40 and is configured to preheat a feed material to a desired temperature prior to introduction of the feed to HSD 40. A reagent source 30 may be fluidly connected with HSD 40 and provide reagent (e.g. gaseous halogen) thereto. High shear system 100 may further comprise a scrubber 60 positioned on an offgas line 55 from gas/liquid separator 50, the scrubber configured to separate a liquid product from a waste gas stream. Each of these components will be described in more detail hereinbelow.

High Shear Device 40.

As mentioned above, the disclosed high shear system comprises at least one high shear device. High shear device 40 is positioned upstream of and fluidly connected with residence time vessel 10 and is configured for subjecting the contents of HSD 40 to high shear, providing a high shear treated stream to residence time vessel 10.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the submicron to about 1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.025 mm to 10 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1 to 25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

The HSD of high shear system 100 comprises at least one revolving element that creates the mechanical force applied to the reactants therein. The HSD comprises at least one stator and at least one rotor separated by a clearance. For example, the rotors can be conical or disk shaped and can be separated from a complementarily-shaped stator. In embodiments, both the rotor and stator comprise a plurality of circumferentially-spaced rings having complementarily-shaped tips. A ring may comprise a solitary surface or tip encircling the rotor or the stator. In embodiments, both the rotor and stator comprise more than 2 circumferentially-spaced rings, more than 3 rings, or more than 4 rings. For example, in embodiments, each of three generators comprises a rotor and stator each having 3 complementary rings, whereby the material processed passes through 9 shear gaps or stages upon traversing HSD 40. Alternatively, each of three generators may comprise four rings, whereby the processed material passes through 12 shear gaps or stages upon passing through HSD 40. In some embodiments, the stator(s) are adjustable to obtain the desired shear gap between the rotor and the stator of each generator (rotor/stator set). Each generator may be driven by any suitable drive system configured for providing the desired rotation.

In some embodiments, HSD 40 comprises a single stage dispersing chamber (i.e. a single rotor/stator combination; a single high shear generator). In some embodiments, HSD 40 is a multiple stage inline disperser and comprises a plurality of generators. In certain embodiments, HSD 40 comprises at least two generators. In other embodiments, HSD 40 comprises at least 3 generators. In some embodiments, HSD 40 is a multistage mixer whereby the shear rate (which varies proportionately with tip speed and inversely with rotor/stator gap width) varies with longitudinal position along the flow pathway, as further described hereinbelow.

According to this disclosure, at least one surface within HSD 40 may be made of, impregnated with, or coated with a catalyst suitable for catalyzing a desired reaction, as described in U.S. patent application Ser. No. 12/476,415, which is hereby incorporated herein by reference for all purposes not contrary to this disclosure.

In some embodiments, the minimum clearance (shear gap width) between the rotor and the stator is in the range of from about 0.025 mm (0.001 inch) to about 3 mm (0.125 inch). The shear gap may be in the range of from about 5 micrometers (0.0002 inch) and about 4 mm (0.016 inch). In embodiments, the shear gap is in the range of 5, 4, 3, 2 or 1 μm. In some embodiments, the minimum clearance (shear gap width) between the rotor and the stator is in the range of from about 1 μm (0.00004 inch) to about 3 mm (0.012 inch). In some embodiments, the minimum clearance (shear gap width) between the rotor and the stator is less than about 10 μm (0.0004 inch), less than about 50 μm (0.002 inch), less than about 100 μm (0.004 inch), less than about 200 μm (0.008 inch), less than about 400 μm (0.016 inch). In certain embodiments, the minimum clearance (shear gap width) between the rotor and the stator is about 1.5 mm (0.06 inch). In certain embodiments, the minimum clearance (shear gap width) between the rotor and the stator is about 0.2 mm (0.008 inch). In certain configurations, the minimum clearance (shear gap) between the rotor and stator is at least 1.7 mm (0.07 inch). The shear rate produced by the HSD may vary with longitudinal position along the flow pathway. In some embodiments, the rotor is set to rotate at a speed commensurate with the diameter of the rotor and the desired tip speed. In some embodiments, the HSD has a fixed clearance (shear gap width) between the rotor and the stator. Alternatively, the HSD has adjustable clearance (shear gap width).

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (meters, for example) times the frequency of revolution (for example revolutions per minute, rpm). The frequency of revolution may be greater than 250 rpm, greater than 500 rpm, greater than 1000 rpm, greater than 5000 rpm, greater than 7500 rpm, greater than 10,000 rpm, greater than 13,000 rpm, or greater than 15,000 rpm. In embodiments, the rotational frequency, flow rate, and temperature may be adjusted to get a desired product profile. If channeling should occur, and reaction is inadequate, the rotational frequency may be increased to minimize undesirable channeling. Alternatively or additionally, high shear treated product from one HSD may be introduced into a second or subsequent HSD 40.

HSD 40 may provide a tip speed in excess of 22.9 m/s (4500 ft/min) and may exceed 40 m/s (7900 ft/min), 50 m/s (9800 ft/min), 100 m/s (19,600 ft/min), 150 m/s (29,500 ft/min), 200 m/s (39,300 ft/min), or even 225 m/s (44,300 ft/min) or greater in certain applications. For the purpose of this disclosure, the term 'high shear' refers to mechanical rotor-stator devices (e.g., colloid mills or rotor-stator dispersers) that are capable of tip speeds in excess of 5.1 m/s (1000 ft/min) or those values provided above and require an external mechanically driven power device to drive energy into the stream of materials to be reacted. By contacting the reactants with the rotating members, which can be made from, coated with, or impregnated with stationary catalyst, significant energy is transferred to the reaction. The energy consumption of HSD 40 will generally be very low.

In some embodiments, HSD 40 is capable of delivering at least 300 L/h at a tip speed of at least 22.9 m/s (4500 ft/min). The power consumption may be about 1.5 kW. HSD 40 combines high tip speed with a very small shear gap to produce significant shear on the material being processed. The amount of shear will be dependent on the viscosity of the fluid in HSD 40. Accordingly, a local region of elevated pressure and temperature is created at the tip of the rotor during operation of HSD 40. In some cases the locally elevated pressure is about 1034.2 MPa (150,000 psi). In some cases the locally elevated temperature is about 500° C. or more. In some cases, these local pressure and temperature elevations may persist for nano- or pico-seconds.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the fluid. In embodiments, the energy expenditure is at least about 1000 W/m$^3$, 5000 W/m$^3$, 7500 W/m$^3$, 1 kW/m$^3$, 500 kW/m$^3$, 1000 kW/m$^3$, 5000 kW/m$^3$, 7500 kW/m$^3$, or greater. In embodiments, the energy expenditure of HSD 40 is greater than 1000 watts per cubic meter of fluid therein. In embodiments, the energy expenditure of HSD 40 is in the range of from about 3000 W/m$^3$ to about 7500 kW/m$^3$. In embodiments, the energy expenditure of HSD 40 is in the range of from about 3000 W/m$^3$ to about 7500 W/m$^3$. The actual energy input needed is a function of what reactions are occurring within the HSD, for example, endothermic and/or exothermic reaction(s), as well as the mechanical energy required for dispersing and mixing feedstock materials. In some applications, the presence of exothermic reaction(s) occurring within the HSD mitigates some or substantially all of the reaction energy needed from the motor input. Of course, when dispersing a gas in a liquid, the energy requirements are significantly less.

The shear rate is the tip speed divided by the shear gap width (minimal clearance between the rotor and stator). The shear rate generated in HSD 40 may be greater than 20,000 s$^{-1}$. In some embodiments the shear rate is at least 30,000 s$^{-1}$ or at least 40,000 s$^{-1}$. In some embodiments the shear rate is greater than 30,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In some embodiments the shear rate is at least 3,000,000 s$^{-1}$. In some embodiments the shear rate is at least 5,000,000 s$^{-1}$. In some embodiments the shear rate is at least 7,000,000 s$^{-1}$. In some embodiments the shear rate is at least 9,000,000 s$^{-1}$. In embodiments where the rotor has a larger diameter, the shear rate may exceed about 9,000,000 s$^{-1}$. In embodiments, the shear rate generated by HSD 40 is in the range of from 20,000 s$^{-1}$ to 10,000,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$.

In some embodiments, HSD 40 comprises a colloid mill. Suitable colloidal mills are manufactured by IKA® Works, Inc. Wilmington, N.C. and APV North America, Inc. Wilmington, Mass., for example. In some instances, HSD 40 comprises the DISPAX REACTOR® of IKA® Works, Inc.

In some embodiments, each stage of the external HSD has interchangeable mixing tools, offering flexibility. For example, the DR 2000/4 DISPAX REACTOR® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for variance of shear rate along the direction of flow. In some embodiments, each of the stages is operated with super-fine generator.

Figure 2:
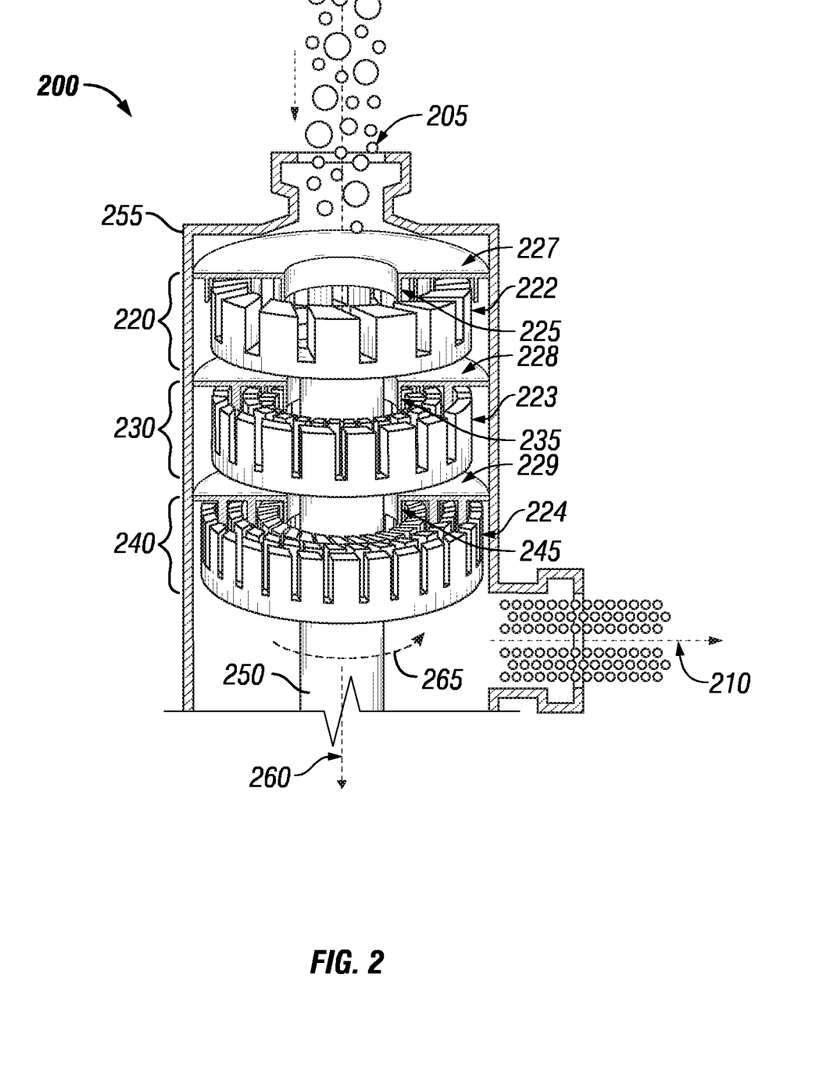
FIG. 2 is a cross-sectional diagram of a high shear device suitable for use in embodiments of the disclosed system and method.

In embodiments, a scaled-up version of the DISPAX® reactor is utilized. For example, in embodiments HSD 40 comprises a SUPER DISPAX REACTOR® DRS 2000. The HSD unit may be a DR 2000/50 unit, having a flow capacity of 125,000 liters per hour, or a DRS 2000/50 having a flow capacity of 40,000 liters/hour. Because residence time is increased in the DRS unit, the fluid therein can be subjected to more shear. Referring now to FIG. 2, there is presented a longitudinal cross-section of a suitable device HSD 200 for use as HSD 40. HSD 200 of FIG. 2 is a dispersing device comprising three stages or rotor-stator combinations, 220, 230, and 240. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 may be fixably coupled to the wall 255 of HSD 200. As mentioned hereinabove, each rotor and stator may comprise rings of complementarily-shaped tips, leading to several shear gaps within each generator.

As mentioned hereinabove, each generator has a shear gap width which is the minimum distance between the rotor and the stator. In the embodiment of FIG. 2, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10 mm. Alternatively, the system comprises an HSD 200 wherein gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. HSD 200 may be configured so that the shear rate remains the same or increases or decreases stepwise longitudinally along the direction of the flow 260.

Generators 220, 230, and 240 may comprise a coarse, medium, fine, and super-fine characterization, having different numbers of complementary rings or stages on the rotors and complementary stators. Rotors 222, 223, and 224 and stators 227, 228, and 229 may be toothed designs. Each generator may comprise two or more sets of complementary rotor-stator rings. In embodiments, rotors 222, 223, and 224 comprise more than 3 sets of complementary rotor/stator rings. In embodiments, the rotor and the stator comprise no teeth, thus forcing the reactants to flow through pores, for example, of a sintered material.

HSD 40 may be a large or small scale device. In embodiments, system 100 is used to process from less than 100 gallons per minute to over 5000 gallons per minute. In embodiments, one or more HSD 40 processes at least 100, 500, 750, 900, 1000, 2000, 3000, 4000, 5000 gpm or more. Large scale units may produce 1000 gal/h (24 barrels/h). The inner diameter of the rotor may be any size suitable for a desired application. In embodiments, the inner diameter of the rotor is from about 12 cm (4 inch) to about 40 cm (15 inch). In embodiments, the diameter of the rotor is about 6 cm (2.4 inch). In embodiments, the outer diameter of the stator is about 15 cm (5.9 inch). In embodiments, the diameter of the stator is about 6.4 cm (2.5 inch). In some embodiments the rotors are larger than or about 6.0 cm (2.4 inch) in diameter and the stators are larger than or about 6.4 cm (2.5 inch) in diameter. The clearance may be less than, greater than, or about 4 mm. In certain embodiments, each of three stages is operated with a super-fine generator (e.g. comprising a gap of between about 0.025 mm and about 3 mm) comprising a number of sets of complementary rotor/stator rings.

HSD 200 is configured for receiving at inlet 205 a fluid mixture from line 13 (of FIG. 1). The mixture comprises reactants, as discussed further hereinbelow. In embodiments, the reactants comprise (a) one or more halogenation and/or sulfonation reagent; and (b) a feed to be sulfonated and/or halogenated, said feed comprising at least one paraffin. The reagent may comprise one or more component selected from halogenating and sulfonating agents, such as halogens, oleum and sulfuric acid. As discussed further hereinbelow, the halogenation/sulfonation reagent may be provided by a reagent source 30 and the feed to be sulfonated/halogenated may be provided via a preheater 20 and line 12. Feed stream entering inlet 205 is pumped serially through generators 220, 230, and then 240, such that a high shear treated product stream is produced. The high shear treated product stream may comprise an emulsion or dispersion. The high shear treated product exits HSD 200 via outlet 210 (line 18 of FIG. 1). The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on the fluid in shear gaps 225, 235, and 245 (and, when present, in the gaps between the rotor and stator teeth) through which fluid flows process the fluid and create the high shear treated product. The product comprises a high shear mixture. The high shear-treated product exits HSD 200 via high shear outlet 210 (line 18 of FIG. 1). Each generator 220, 230, 240 of high shear device 200 may comprise interchangeable rotor-stator combinations for producing a narrow distribution of a desired bubble size, if feedstream 205 comprises a gas, or globule size, if feedstream 205 comprises a liquid, in the high shear treated stream 210 (e.g. product dispersion or emulsion).

High shear device 200 is fed a reaction mixture comprising the feed stream 205. Feed stream 205 may comprise an emulsion of a dispersible reagent phase in a continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term 'emulsion' encompasses continuous phases comprising gas bubbles, continuous phases comprising particles (e.g., solid catalyst), continuous phases comprising droplets of a fluid that is substantially insoluble in the continuous phase, and combinations thereof.

As mentioned above, in certain instances, HSD 200 comprises a DISPAX REACTOR® of IKA® Works, Inc. Wilmington, N.C. and APV North America, Inc. Wilmington, Mass. Several models are available having various inlet/outlet connections, horsepower, tip speeds, output rpm, and flow rate. Selection of the HSD will depend on throughput selection, for example. IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2 HP power, output speed of 7900 rpm, flow capacity (water) approximately 300-700 L/h (depending on generator), a tip speed of from 9.4-41 m/s (1850 ft/min to 8070 ft/min). Scale up may be performed by using a plurality of HSDs, or by utilizing larger HSDs. Scale-up using larger models is readily performed, and results from larger HSD units may provide improved efficiency in some instances relative to the efficiency of lab-scale devices. The large scale unit may be a DISPAX® 2000/unit. For example, the DRS 2000/5 unit has an inlet size of 51 mm (2 inches) and an outlet of 38 mm (1.5 inches).

In embodiments HSD 40 or portions thereof are manufactured from refractory/corrosion resistant materials. For example, sintered metals, INCONEL® alloys, HASTELLOY® materials may be used. For example, when the mixture is caustic to the rotors, stators, and/or other components of HSD 40 may be manufactured of refractory materials (e.g. sintered metal) in various applications. This may be desirable, for example, when the system is utilized for sulfonation.

The high shear treated product in 210 may comprise a dispersion of gas particles, or bubbles, in a liquid. In embodiments, the high shear treated product 210 comprises a dispersion or emulsion of a previously immiscible or insoluble gas, liquid or solid in a continuous phase. In embodiments, the high shear treated product 210 comprises gas bubbles having an average gas particle or bubble diameter of less than about 1.5 μm. In embodiments, the bubbles are sub-micron in mean diameter size. In certain instances, the average bubble size is in the range from about 1.0 μm to about 0.1 μm. In embodiments, the average bubble size is less than about 400 nm (0.4 μm) or less than about 100 nm (0.1 μm).

Tip speed is the velocity (m/sec) associated with the end of one or more revolving element that is transmitting energy to the reactants. Tip speed, for a rotating element, is the circumferential distance traveled by the tip of the rotor per unit of time, and is generally defined by the equation V (e.g. in m/sec)=$\pi \cdot D \cdot n$, where V is the tip speed, D is the diameter of the rotor (e.g. in meters), and n is the rotational speed of the rotor (e.g. in revolutions per second). Tip speed is thus a function of the rotor diameter and the rotation rate.

For colloid mills, typical tip speeds are in excess of 23 m/sec (4500 ft/min) and can exceed 40 ms/ec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi). The local pressure during operation further depends on the tip speed, fluid viscosity, and the rotor-stator gap.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the fluid. In embodiments, the energy expenditure is at least about 1000 W/m$^3$, 5000 W/m$^3$, 7500 W/m$^3$, 1 kW/m$^3$, 500 kW/m$^3$, 1000 kW/m$^3$, 5000 kW/m$^3$, 7500 kW/m$^3$, or greater. In embodiments, the energy expenditure of HSD 40 is greater than about 1000 watts per cubic meter of fluid therein. In embodiments, the energy expenditure of HSD 40 is in the range of from about 3000 W/m$^3$ to about 7500 kW/m$^3$. In embodiments, the energy expenditure of HSD 40 is in the range of from about 3000 W/m$^3$ to about 7500 W/m$^3$. The actual energy input needed is a function of what reactions are occurring within the HSD, for example, endothermic and/or exothermic reaction(s), as well as the mechanical energy required for dispersing and mixing feedstock materials. In some applications, the presence of exothermic reaction(s) occurring within the HSD mitigates some or substantially all of the reaction energy needed from the motor input. When dispersing a gas in a liquid, the energy requirements are significantly less.

High shear device 200 combines high tip speeds with a very small shear gap to produce significant shear on the material. The amount of shear is typically dependent on the viscosity of the fluid. The shear rate generated in high shear device 200/40 may be greater than 20,000 s$^{-1}$, 30,000 s$^{-1}$, 40,000 s$^{-1}$, 50,000 s$^{-1}$, or 60,000 s$^{-1}$. In embodiments, the shear rate generated is in the range of from about 20,000 s$^{-1}$ to 100,000 s$^{-1}$.

In embodiments, the high shear device 200 produces a gas emulsion capable of remaining dispersed at atmospheric pressure for at least about 15 minutes. The high shear treated product may comprise an emulsion of gas particles or bubbles that are less than about 1.5 μm in diameter. Not to be limited by a specific theory, it is known in emulsion chemistry that sub-micron particles, or bubbles, dispersed in a liquid undergo movement primarily through Brownian motion effects. The bubbles in the high shear treated product 210 created by high shear device 200 may have greater mobility through boundary layers, thereby facilitating and accelerating the reaction through enhanced transport of reactants.

The rotor is set to rotate at a speed commensurate with the diameter of the rotor and the desired tip speed as described hereinabove. In embodiments, transport resistance is reduced by incorporation of high shear device 200 such that the velocity of the reaction is increased by at least about 5%. Alternatively, high shear device 200 comprises a high shear colloid mill that serves as an accelerated rate reactor. The accelerated rate reactor may comprise a single stage dispersing chamber or may be a multiple stage inline disperser comprising at least 2 stages.

Selection of high shear device 200 is dependent on throughput requirements and desired particle or bubble size in high shear treated product 210. In certain instances, high shear device 200 comprises a DISPAX REACTOR® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 L/h to approximately 700 l/h (depending on generator), a tip speed of from 9.4 m/s to about 41 m/s (about 1850 ft/min to about 8070 ft/min). Several alternative models are available having various inlet/outlet connections, horsepower, tip speeds, output rpm, and flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. For example, the rate of chlorination increases with increasing temperature. Chlorination consists essentially of two stages, the absorption of chlorine and the successive rapid substitution reactions. The rate controlling factor is thus diffusion. As the viscosity of the reaction product increases during the course of chlorination, an increase in temperature results in an increase in diffusivity and, thus, an increase in the rate of chlorination. The localized increases in temperature provided by the HSD may thus enhance the rate of halogenation (e.g. chlorination), especially at the end process, when the viscosity of the product is higher.

Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods is operated under what are believed to be cavitation conditions effective to dissociate the reactants into free radicals for the formation of the halogenated and/or sulfonated paraffin product.

Residence Time Vessel 10.

The disclosed high shear system comprises a residence time vessel 10. Residence time vessel 10 is fluidly connected with HSD 40 such that high shear treated product exiting HSD 40 may be introduced into vessel 10. Line 18 may fluidly connect HSD 40 with residence time vessel 10. Vessel 10 may be cooled, for example, via a heat exchanger. Direct injection of coolant (i.e. cooling water and/or fresh feedstock) into the high shear-treated stream (e.g. a chlorinated stream) is also used to control temperature, in embodiments. Cooling water 15 may be heated by heat transfer with the contents of residence time vessel 10. One or more valves 17 may be configured to control the flow of cooling water to residence time vessel 10, and thus control the temperature of the material removed therefrom (i.e. via line 16). One or more temperature transmitters may be utilized to determine desirable operation of valve(s) 17. For example temperature transmitters TT2 and TT3 may be positioned on the high shear treated product outlet line 18 and/or on product line 16.

It is also envisaged that, in embodiments, residence time vessel 10 is absent and high shear treated product from HSD 40 is suitably cooled via one or more heat exchangers positioned on line 18 between HSD 40 and phase separator 50.

Phase Separator 50.

High shear system 100 further comprises phase separator 50. Phase separator 50 is any apparatus known to one of skill in the art to be operable to separate gas from liquid (sulfonated and/or halogenated) product. Line 16 is configured for introduction of cooled product from residence time vessel 10 into phase (e.g. gas/liquids) separator 50. An exit line 55 is configured for removal of gas from gas/liquids separator 50 and an exit line 75 is configured for removal of liquid product from gas/liquids separator 50. Recycle line 75 may fluidly connect gas/liquid separator 50 and HSD 40, such that a portion of the product in line 75 may be returned to HSD 40 (for example, via pump 5). A line 80 may be configured to remove sulfonated and/or halogenated product from high shear system 100.

Pump(s) 5.

As mentioned hereinabove, high shear system 100 may comprise one or more pumps 5. In the embodiment of FIG. 1, pump 5 is positioned on exit line 75 from phase separator 50. Pump 5 can be configured for either continuous or semi-continuous operation, and may be any suitable pumping device that is capable of providing controlled flow through HSD 40 and high shear system 100. In applications, pump 5 provides greater than 202.65 kPa (2 atm) pressure or greater than 303.97 kPa (3 atm) pressure. Pump 5 may be a Roper Type 1 gear pump, Roper Pump Company (Commerce Ga.) Dayton Pressure Booster Pump Model 2P372E, Dayton Electric Co (Niles, Ill.) is one suitable pump. In some embodiments of the system, pump 5 is capable of pressures greater than about 2026.5 kPa (20 atm). In addition to pump 5, one or more additional, high pressure pumps may be included in the system illustrated in FIG. 1. For example, a pump, which may be similar to pump 5, may be included on flow line 18 and/or flow line 16 for controlling flow/pressure.

Pump(s) 5 may thus build pressure throughout HSS 100. In this way, HSS 100 can combine high shear with pressure to enhance reactant intimate mixing. All contact parts of pump(s) 5 can be made of refractory materials, such as stainless steel, for example, 316 stainless steel. Such refractory materials of construction for pump(s) 5 may be particularly suitable for halogenation of paraffins, for example, for chlorination in which HCl is produced as a byproduct.

One or more pressure transmitters can be positioned throughout system 100 to measure the pressure therein. For example, in the embodiment of FIG. 1, a pressure transmitter PT1 is positioned on feed line 12. Other suitable locations for pressure measurement device(s) include on line 25, line 13, line 18, line 16, or any combination thereof. Operation of the one or more pump(s) 5 may be adjusted in response to the measured pressure measurements and the desired pressures.

Heat Transfer Devices and Flow Control.

Internal or external heat transfer devices or apparatus are also contemplated in variations of the system. As mentioned hereinabove, for example, residence time vessel 10 may be temperature controlled via heart exchange with cooling water introduced thereto via heat exchanger fluid inlet line 15. The flow of cooling water may be controlled by one or more valve(s) 17, in response to the temperatures of material entering and exiting residence time vessel 10, said temperatures of entering and/or exiting material being measured by temperature transmitters TT2 and TT3, respectively.

High shear system 100 may further comprise a preheater 20 configured to adjust the temperature of the feed material (to be halogenated and/or sulfonated) as desired prior to introduction into HSD 40. For example, when high shear system 100 is utilized for halogenation and/or sulfonation of a paraffin wax (which is solid at room temperature), one or more preheaters 20 may be configured to melt the wax and heat it to a desired temperature prior to introduction into HSD 40. Line 11 may introduce (relatively cold) feed material into preheater 20 and line 12 may fluidly connect preheater 20 with HSD 40. A temperature transmitter TT1 may be positioned on heated feed line 12, to determine the temperature thereof, and the heating provided by preheater 20 adjusted as needed to provide a desired temperature of the preheated feed material. In embodiments, preheater 20 is configured to preheat the feed material to a temperature in the range of from about 40° C. to about 180° C., from about 50° C. to about 150° C., or from about 60° C. to about 130° C. In embodiments wherein the feed material comprises a wax that is a solid at room temperature, the minimum temperature is the lowest temperature at which the wax melts and flows. Preheater 20 may heat the feed material via any method known to one skilled in the art.

Other suitable locations for one or more heat transfer devices are within residence time vessel 10, between RTV 10 and HSD 40, between pump 5 and HSD 40, between RTV 10 and G/L separator 50, and on flow line 75 when fluid in G/L separator 50 product outlet line 75 is recycled to HSD 40. In the embodiment of FIG. 1, preheater 20 is positioned on line 11 to maintain the feed as a fluid at a desired temperature. HSD 40 may comprise an inner shaft which may be cooled, for example water-cooled, to partially or completely control the temperature within the HSD. Some non-limiting examples of suitable heat transfer devices are shell, tube, plate, and coil heat exchangers, as known in the art.

One or more flow control valves or FCVs may be positioned throughout system 100 to control the flow therethrough. For example, a flow control valve FCV1 may be positioned on sulfonation/halogenation reagent inlet line 22 to control the flow of reagent. Should the temperature within system 100 be too high, as measured for example via TT2 and/or TT3, flow through reagent line 22 may be reduced accordingly by adjustment of FCV1. A flow control valve FCV2 may be positioned on feed line 12 to control the flow of feed material into HSD 40. Flow control valves FCV3 and/or FCV4 may be positioned on recycle line 25 and product line 80, respectively, to control the amount of material recycled to HSD 40. FCV2 and FCV1 may be configured to provide at least a minimum flow of feed material in line 12 and sulfonation/halogenation reagent in line 22, respectively, such that at least a minimum desired flow of material is provided to HSD 40 via HSD inlet line 13, as indicated in the schematic of FIG. 1.

Offgas Recovery Apparatus 60.

High shear system 100 may further comprise offgas recovery apparatus 60. Offgas recovery apparatus 60 can comprise one or more suitable apparatus for removing or neutralizing at least one component from the gas exiting gas/liquids separator 50. In embodiments, offgas recovery apparatus 60 comprises a scrubber. Offgas recovery apparatus 60 may comprise a wet scrubber, a dry scrubber, or both. Offgas recovery aid is introduced via line 85. The recovery aid may comprise, for example, water. Offgas recovery apparatus 60 comprises an outlet line 65 for neutralized and/or component-reduced offgas (which, in embodiments, is suitable for venting to the atmosphere) and an outlet line 70 for a stream comprising a removed component and/or recovery aid (e.g. scrubbing material). In embodiments in which high shear system 100 is configured for chlorination, offgas recovery apparatus 60 comprises an outlet 70 for aqueous hydrochloric acid, as will be discussed further hereinbelow. In embodiments, offgas recovery apparatus 60 comprises distillation apparatus. In embodiments, water is introduced via line 85 and aqueous hydrochloric acid (liquid) is removed via line 70. Offgas recovery apparatus 60 may be configured for the production of aqueous hydrochloric acid having from about 10 to about 80, from about 20 to about 75, or from about 30 to about 70 weight percent hydrochloric acid.

Method for the Production of Sulfonated and/or Halogenated Paraffin.

The high shear paraffin halogenation and/or sulfonation method will now be described in relation to FIG. 1 which is a representative process flow diagram of a high shear system (HSS) 100 for the production of halogenated and/or sulfonated paraffin from feed comprising paraffin and reagent(s) selected from halogenating and sulfonating agents. The term 'treated' as used hereinbelow is intended to mean halogenated, sulfonated, or sulfo-halogenated. Desirably, the method is continuously operated (i.e. not batchwise).

Feed material to be treated and reagent are introduced into HSD 40 via inlet line 13. The feed material to be treated comprises at least one paraffin. The feed material may comprise at least one selected from the group consisting of normal paraffins (NP). In embodiments, the feed material comprises n-decane. The term 'normal paraffin' refers to paraffin having the characteristics presented in Table 1 below.

TABLE 1

| Properties of Normal Paraffin (NP) | |
|---|---|
| Parameter | Value |
| Specific Gravity at 15.5° C. | 0.74-0.76 |
| Total normal paraffins (%) | ≥95 |
| Flash Point (° C.) | 65 |
| Carbon Distribution (%): | |
| ≤C9 | ≤2.0 |
| C10 | ≤15 |
| C11-C13 | ≥85 |
| ≥C14 | ≤5 |

In embodiments, the feed material comprises at least one selected from light normal paraffins (LNP). The term 'light normal paraffin' refers to paraffin having the characteristics in Table 2 below.

TABLE 2

| Properties of Light Normal Paraffin (LNP) | |
|---|---|
| Parameter | Value |
| Specific Gravity at 15.5° C. | 0.73-0.75 |
| Flash Point (° C.) | 43 |
| Carbon Distribution (%): | |
| ≤C8 | ≤2 |
| C9 | 35-60 |
| C10 | 32-45 |
| C11 | 5-30 |
| C12 | ≤2 |

In embodiments, the feed material comprises raw paraffin. As used herein, the term 'raw paraffin' refers to a mixture of normal paraffin and light normal paraffin. In embodiments, the feed material comprises at least one selected from the group consisting of polyethylene waxes. The feed material may comprise paraffinic oil, paraffinic wax, polyethylene wax, or any combination thereof. The feed material can comprise liquid normal paraffins, paraffin wax, or a combination thereof. In embodiments, the feed material comprises one or more selected from linear paraffins having more than 9 carbon atoms. In embodiments, the majority of the feed material comprises one or more selected from linear paraffins having from about 9 to about 15 carbon atoms. In embodiments, the feed material comprises high-paraffin petroleum fraction and/or paraffin waxes melting in the 50-60° C. temperature range. In embodiments, the feed material comprises paraffin slab wax. The paraffin slab wax may have a melting point of about 55° C. In embodiments, the feed material comprises paraffin produced via Fischer-Tropsch synthesis. The feed material may be a slab wax comprising an oil content in the range of from about 0.3 to about 3.3 wt %. The grade of the resulting halogenated product (e.g. chloroparaffin) will depend on the oil content of the feed material. Generally, a decrease in density, average molecular weight, viscosity measured at 100° C. and resistivity measured at 25° C. may be expected with increasing oil content of the feed material.

As will be understood by those of skill in the art, the disclosed halogenation method may also be applied to thermal halogenations of other organic substances comprising a plurality of hydrogen atoms which can be substituted by halogen atoms. The feed material may be preheated as desired within one or more preheaters 20. For example, relatively 'cold' feed material may be introduced into preheater(s) 20 via line 11, heated within preheater(s) 20 to a desired preheat temperature within preheater(s) 20 and subsequently introduced via feed material inlet line 12 (which may be 'hot' relative to feed material introduced into preheater(s) 20 via line 11) and HSD inlet line 13 into HSD 40. In embodiments, the feed material is heated to a temperature of at least or about 25° C., 30° C., 40° C., 50° C., 60° C., 70° C., or 80° C. In embodiments, the feed material is preheated, within one or more preheaters 20, to a temperature in the range of from about 40° C. to about 180° C., from about 50° C. to about 150° C., or in the range of from about 60° C. to about 130° C. In the case of waxes used as feed material, the minimum temperature is one at which the wax melts and flows. For example, the feed material may comprise polypropylene wax which may have a melt temperature of about 180° C. The feed may comprise a paraffin that is solid/semi-solid at room temperature. In such applications, the solid paraffin may be dissolved in solvent prior to halogenation/sulfonation (e.g. prior to chlorinating). Such use of solvent may facilitate avoidance and/or minimization of excessive temperatures during exothermic reaction.

The feed material is intimately mixed with a suitable reagent (i.e. a halogenation and/or sulfonation reagent) within HSD 40. In embodiments, feed material is mixed with an amount of reagent approximately equal to, slightly in excess of or in excess of the stoichiometric quantity required to halogenate and/or sulfonate the paraffin in the feed to a desired degree. In applications in which the disclosed method is utilized for halogenation, the reagent may be selected from halogens. The reagent may be gaseous, liquid or a combination thereof. For example, in chlorination applications, the reagent may comprise chlorine (e.g. chlorine gas). In embodiments, the molar ratio of chlorine to paraffin supplied is in the range of from about 0.1:1 and 5:1, in the range of from about 0.1:1 and 3:1, or in the range of from about 0.1:1 and 0.3:1. The reagent may be supplied to HSD 40 via a reagent storage apparatus 30. For example, in chlorination applications, reagent storage apparatus 30 may comprise a tanner cylinder or a liquid chlorine flask. Reagent may be introduced into HSD 40 from reagent source 30 by combination in HSD inlet line 13 with feed material from feed material line 12 via reagent line 22.

In the embodiment of FIG. 1, reagent and feed material are combined, via lines 22 and 12 respectively, and introduced into HSD 40 via HSD inlet line 13, which is in fluid communication with high shear device 40. In certain applications, reagent in line 22 is introduced or injected directly into HSD 40. In embodiments reagent may be continuously combined with feed material in line 12 to form HSD feed material in line 13. In embodiments, HSD feed material in line 13 is formed from a combination of halogen gas and paraffinic feed material to be treated. In embodiments, reagent (which may be a dispersible gas) in line 22 and feed material in line 12 are injected separately into HSD 40 for processing by high shear device 40. Furthermore, any suitable halogenation/sulfonation catalyst known to those of skill in the art may also be introduced into HSD 40. In certain instances, the catalyst introduced comprises a Lewis acid catalyst. The catalyst may be chosen from metallic chlorides and iodine. In embodiments, a homogeneous catalyst is selected from iodine, phosphorus, sulfur, antimony chloride, iron chloride, zinc chloride, and combinations thereof.

In embodiments, the disclosed method is utilized to produce halogenated paraffin (e.g. chlorinated paraffin wax). In embodiments, the feed material comprises one or more paraffinic hydrocarbon having from about 8 to about 24 carbons. The halogenation may be carried out in the presence of any suitable stabilizer known in the art to inhibit dehydrochlorination and/or hydrolysis. Suitable stabilizers include various bases, e.g. triethylamine, triethanolamine, pyridine and pyridine-type cyclic compounds. In embodiments, chlorination is carried out in the presence of one or more stabilizers, such as taught in PCT Patent App. No. PCT/IN2009/000205, which is hereby incorporated herein by reference in its entirety for all purposes not contrary to this disclosure. In such embodiments, the stabilizer may be introduced into or present within HSD 40 and/or residence time vessel 10 at a concentration in the range of from about 100-1500 ppm. One or more stabilizer (e.g. activity control agent) may be selected from the group consisting of organo tin compounds and mercaptides, carboxylates, sulfides and maleates of Group II and Group 14 metals which may be suitable for use in paraffin chlorination. The activity control agent may be any additive, promoter, accelerator or catalyst that, when used in paraffin halogenation reaction, improves the heat stability of the halogenated product and/or increases the rate of reaction.

HSD 40 serves to intimately mix the feed material to be treated with the reagent(s) and optionally suitable catalyst. As discussed in detail above, high shear device 40 is a mechanical device that utilizes, for example, a stator rotor mixing head with a fixed gap between the stator and rotor. Within high shear device 40, reagent and feed material to be treated are intimately mixed. In embodiments, within HSD 40, an emulsion or dispersion comprising microbubbles and/or nanobubbles of reagent gas is produced. In embodiments, the resultant dispersion comprises bubbles having a mean diameter in the submicron size. In embodiments, the resultant dispersion has an average bubble size of less than about 1.5 μm. In embodiments, the mean bubble size is less than from about 0.1 μm to about 1.5 μm. Not to be limited by a specific method, it is known in emulsion chemistry that submicron particles dispersed in a liquid undergo movement primarily through Brownian motion effects. Thus it is believed that submicron gas particles created by high shear device 40 reduce mass transfer resistance to reaction, thereby facilitating and accelerating the halogenation and/or sulfonation reaction(s). In embodiments, the high shear mixing produces gas bubbles capable of remaining dispersed at atmospheric pressure for about 15 minutes or longer depending on the bubble size. In embodiments, the mean bubble size is less than about 400 nm or less than about 100 nm. In chlorination applications, for example, HSD 40 may serve to create a dispersion of chlorine bubbles. The emulsion may be considered a micro-foam.

A high shear treated product exits HSD 40 by HSD outlet line 18. The high shear treated product in line 18 may be introduced into residence time vessel 10. Within residence time vessel 10, the high shear treated product is allowed to continue reaction and/or may be cooled. As the halogenation/sulfonation reaction(s) may be exothermic, residence time vessel 10 may be cooled, for example, by introduction of cooling water to residence time vessel 10 via heat exchange fluid inlet line 15 and heat exchange with the high shear treated product. In embodiments, residence time vessel 10 is configured for halogenated and/or sulfonated paraffin production. As mentioned hereinabove, residence time vessel 10 may further comprise temperature control (i.e. heat exchanger), stirring system, and/or level regulator(s) as known to those of skill in the art. In embodiments, one or more inlets are fluidly coupled to residence time vessel 10, such that additional material (e.g. catalyst for catalyzing the halogenation/sulfonation) may be added directly thereto. In embodiments, production is continuous within residence time vessel 10. Product is removed from residence time vessel 10 via product outlet line 16.

A specified reaction temperature may be maintained in residence time vessel 10, as known to those of skill in the art. In certain embodiments, the reactor includes internally or externally positioned heat exchangers. Alternatively, heat exchangers may be positioned in any location along the production stream within high shear system (HSS) 100. Suitable locations for external heat transfer devices include between the pump 5 and high shear mixer 40, between HSD 40 and residence time vessel 10, and between residence time vessel 10 and further downstream processing systems. There are many types of heat transfer devices that may be suitable; such exchangers might include shell and tube, plate, and coil heat exchangers without limitation. Further heat exchangers may be known to one skilled in the art.

In embodiments, halogenation (e.g. chlorination) is carried out at temperature(s) of less than about 150° C. In embodiments, halogenation (e.g. chlorination) is carried out at a temperature in the range of from about 25° C. to about 200° C., from about 60° C. to about 150° C., from about 90° C. to about 170° C., from about 90° C. to about 150° C., or from about 100° C. to about 150° C. In embodiments, the pressure within residence time vessel 10 or throughout system 100 is less than, approximately equal to, or up to a few (e.g. up to about 1, 2 or 3) atmospheres above atmospheric pressure. In embodiments, chlorination of paraffin feed material is carried out at a temperature in the range of from about 60° C. to 120° C. and/or a pressure of approximately 1 atmosphere.

In embodiments, the residence time within HSD 40 will be on the order of seconds. In embodiments, the residence time within HSD 40 is less than 0.5 minutes and/or is in the range of from about 0.001 min to about 0.2 min, from about 0.005 min to about 0.1 min, or from about 0.05 min to about 0.1 min. For example, at six GPM and a high shear capacity of 0.1 GAL, the residence time in HSD 40 may be approximately one second. In embodiments, the residence time within residence time vessel 10 is less than about 8 hr, less than about 4 hr, or less than about 1 hr.

Material is removed from residence time vessel 10 via outlet line 16 and may be introduced into gas/liquids separator 50. Within gas/liquids separator 50, gas is separated from the product comprising halogenated and/or sulfonated paraffin(s). Gas, which may comprise unreacted halogen, gaseous byproduct (e.g., hydrogen chloride in the case of chlorination), or low boiling product is removed via gas line 55. The liquid product from which gas has been separated is removed from gas/liquids separator 50 via non-gaseous product line 75.

Gas separated within gas/liquids separator 50 may be introduced into offgas recovery apparatus 60. Offgas recovery apparatus 60 may comprise, for example, scrubbing apparatus. Offgas recovery apparatus 60 serves to remove and/or neutralize a component from/of the gas removed from gas/liquids separator 50 via gas line 55. For example, in the case of chlorination, a scrubber within offgas recovery apparatus 60 may serve to produce aqueous hydrochloric acid from the HCl gas in line 55. An offgas is removed from offgas recovery apparatus 60 via offgas outlet line 65. Offgas recovery agent is introduced into offgas recovery system 60 via line 85. Such offgas recovery agent may comprise a scrubbing agent such as water. Neutralization agent and/or removed component(s) are removed from offgas recovery apparatus 60 via line 70. In embodiments in which system 100 is utilized for chlorination, for example, aqueous hydrochloric acid may be scrubbed from the gas introduced into offgas recovery apparatus 60 via line 55. As discussed further hereinbelow, water may be introduced into offgas recovery apparatus 60 (e.g. scrubber) via line 85 and aqueous hydrochloric acid may be removed from offgas recovery apparatus 60 via outlet line 70. Offgas from which HCl (g) has been scrubbed out may be removed from offgas recovery apparatus 60 via offgas outlet line 65. As offgas recovery apparatus 60 can comprise wet or dry scrubbing apparatus in various embodiments, outlet line 70 may be configured for solid and/or liquid removal from offgas recovery apparatus 60.

Product removed from phase separator 50 via product line 75 may be pumped via pump 5 to product outlet line 80. A portion of the product removed from gas/liquids separator 50 via line 75 may be recycled to HSD 40 via recycle line 25 and HSD inlet line 13.

During operation, the temperature throughout system 100 may be controlled as known in the art. For example, temperature transmitters TT1, TT2 and TT3 may be utilized to determine the temperature of the preheated feed material in line 12, the high shear treated product exiting HSD 40 via HSD outlet line 18, and the temperature of the cooled product exiting residence time vessel 10, respectively, or any combination of TT1, TT2 and/or TT3 may be utilized. Should the temperature of the product be undesirably high (which could lead to undesirable decomposition of the halogenated/sulfonated product), the amount of reagent (e.g. chlorine gas) introduced into HSD 40 may be reduced by, for example, reducing or terminating the flow of reagent through FCV1, adjusting (i.e. reducing) the flow of feed material introduced into HSD 40 via line 12 by adjusting the flow through FCV2, adjusting (i.e. increasing) the flow of recycled material returned via recycle line 25 by adjusting the flow through FCV3 and/or FCV4, and/or adjusting the flow of cooling fluid (e.g. water) throughout system 100 (e.g. to residence time vessel 10 via heat exchange fluid (e.g. cooling water, CW) inlet line 15).

In embodiments, the temperature within residence time vessel 10 is maintained at a temperature in the range of from about ambient or room temperature to about 180° C., in the range of from about 50° C. to about 150° C., or in the range of from about 60° C. to about 130° C. In embodiments in which the feed material comprises one or more wax that is a solid at room temperature, the minimum temperature is one at which the wax remains melted (i.e. melts and flows).

As indicated in FIG. 1, system 100 may be designed such that when flow control valves FCV1, FCV2, FCV3 and/or FCV4 are closed, a minimum desired flow is maintained through bypass valves V1, V2, V3 and/or V4.

The pressure within system 100 may be measured via one or more pressure transmitters. For example, PT1 may be situated on feed material inlet line 12. The pressure may be adjusted via one or more pumps 5 based on the measured pressure. In embodiments, the pressure within residence time vessel 10 is maintained at a pressure in the range of from about atmospheric pressure to about 100 psi, from about atmospheric pressure to about 60 psi, or from about atmospheric pressure to about 30 psig.

In embodiments, the product removed from high shear system 100 via line 18, 16 and/or 75 comprises halogenated paraffin. In embodiments, the product removed from high shear system 100 via line 18, 16 and/or 75 comprises chlorinated paraffin. In embodiments, the product removed from high shear system 100 via line 18, 16 and/or 75 comprises brominated paraffins. In embodiments, the product removed from high shear system 100 via line 18, 16 and/or 75 comprises sulfonated paraffin. In embodiments, the product removed from high shear system 100 via line 18, 16 and/or 75 comprises sulfo-halogenated paraffin.

The system and method of this disclosure may be utilized to produce chlorinated paraffin wax or polychlorinated alkenes having a formula $C_6H_{(2x-n+2)}Cl_2$. In such embodiments, the feed material may comprise liquid n-alkenes and/or paraffin wax. In such applications, 30-70% HCl may be generated as the byproduct of chlorination. In embodiments, aqueous HCl is removed from offgas recovery apparatus 60 via line 70. The aqueous HCl can have a chlorine concentration of from about 30 to 70 weight %. In embodiments, the aqueous HCl removed in line 70 is at least 30 wt %, 31 wt % or at least 32 wt % HCl. The chlorinated products may comprise short chain length (C10-C13); medium chain length (C14-C17); and/or long chain length (C18-C30) chlorinated products. In embodiments, the system may further comprise a fractionator whereby the product may be separated according to chain length. In such instances, fractions comprising short, medium, and/or long chain length products may be separated from the high shear treated product exiting HSD 40. Generally, the chain length of the properties will be dependent on the chain length of the feed material to be treated. In embodiments, product comprising primarily short chain length chlorinated paraffin is produced by utilizing a feed material having a primary chain length in the range of from about C10-C13. In embodiments, product comprising primarily medium chain length chlorinated paraffins is produced by utilizing a feed material having a primary chain length in the range of from about C14 to C17. The properties of the chlorinated product will also depend on the chlorine content (i.e. the amount of chlorine introduced into HSD 40). Similar operation may be utilized to produce other halogenated and/or sulfonated products. In embodiments, the disclosed system and method are utilized to produce a halogenated paraffin product comprising from about 5 wt % to about 65 wt % halogen (e.g. chlorine), from about 6 wt % to about 52 wt % halogen, or from about 42 wt % to about 52 wt % halogen. In embodiments, the disclosed system and method are utilized to produce a chlorinated paraffin product comprising from about 10 wt % to about 70 wt % chlorine, about 10 wt % chlorine, about 42 wt % chlorine, or about 70 wt % chlorine.

In embodiments, the solubility of the chlorinated product is in the range of from about 1.7 to about 236 micrograms/L at 25° C. The pH of the chlorinated product may be in the range of from about 5 to about 7.2. In embodiments, the chlorinated paraffin wax product is substantially soluble in petroleum, petroleum products and organic solvents. In embodiments, the chlorinated paraffin wax product is substantially soluble in esters, ether, chlorinated hydrocarbons, ketones (perhaps excluding acetone) and/or hydrocarbons. The solubility of the chlorinated product is dependent on the chlorine content thereof.

In embodiments, the product comprises chlorinated paraffins that are compatible with most resins, plastics, and a wide range of plasticizers. The chlorinated paraffin may be relatively inert, non-corrosive, and/or have substantial resistance to acids, alkali or both.

In embodiments, the treated product has a density of at least about 1, 1.1, 1.2 or 1.3 $g/cm^3$. The product chlorinated paraffin may have one or more specifications similar to or substantially equivalent to those provided in Table 3 below.

TABLE 3

Properties of Exemplary Chlorinated Paraffin

| | 45 Wt % Chlorinated Paraffin Oil | 52 Wt % Chlorinated Paraffin Oil |
|---|---|---|
| Formula (mol) | $C_nH_{(2n-4)}Cl_n$, where $10 \leq n \leq 15$ | $C_nH_{(2n-4)}Cl_n$, where $10 \leq n \leq 15$ |
| Structure | | |
| Molecular Weight | 350-450 | 350-450 |
| Appearance | Water White to Pale Yellow Viscous Liquid | |
| Density at 25° C., $g/cm^3$ | 1.18 ± 0.05 | 1.25-1.29 |
| Viscosity at 25° C., Poise | 12-20 | 15-22 |
| Packing (HM/HDPEdrum/MSdrum) | 240 kg/drum | 250 kg/drum |
| Maximum Free HCl, % | 0.05 | 0.05 |
| Max. Moisture Content, % | 0.05 | 0.05 |
| Color Stability at 180° C. for 15 min. | Stable | Stable |
| Loss of Volatile Matter (max. %): AL | | |
| 1. 24 h at 100° C. | 0.3 | 0.3 |
| 2. 4 h at 150° C. | 0.6 | 0.6 |
| Fresh Point Open Cup | >450° C. | >450° C. |
| Packaging | 210 L HMNDPE Drums/MS drums | 210 L HMNDPE Drums/MS Drums |

In embodiments, the system and method are utilized to produce chlorinated paraffin wax (CPW) having a density of about 1400 $kg/m^3$. The CPW may be crystal white in color. In embodiments, feed material comprising NP and LNP and PE oil (e.g. at a ratio of NP+LNP to PE oil of about 7:3) is chlorinated in the presence of chlorine gas reagent to produce CPW and HCl gas. As the chlorination is exothermic, the liquid phase chlorination may be conducted at a temperature up to 150° C. For chlorination of paraffins/paraffin wax, HSD 40, residence time vessel 10, phase separator 50, and pipelines connecting such apparatus or any combination thereof may be made of or lined with refractory materials. For example, the pipelines may be made of fiber reinforced plastic (FRP) and/or vessel 10 may be made of mild steel. In embodiments, the disclosed method is utilized for liquid phase chlorination to produce a product from high shear system 100 comprising chlorinated paraffins having one or more properties comparable to or substantially equivalent to those presented in Table 4 below.

TABLE 4

Specification of Chlorinated Paraffin Product

| Characteristic | Product | | |
| --- | --- | --- | --- |
| | CP - 42 | CP - 52 | CP - 62 |
| Appearance | Clear, Oily/Viscous Liquid | | |
| Color, on Gr. Scale, Max | 1 | 1 | 1 |
| Specific Gravity at 25° C. | 1.140-1.175 | 1.260-1.280 | 1.430-1.450 |
| Chlorine Content | 41.0-44.0 | 50.0-53.0 | 62.0-65.0 |
| Heat Stability | | Pass | |
| Volatile Loss, Max. % 180° C./h | 0.50 | 0.50 | 0.50 |
| Viscosity at 25° C., Poise | 1-3 | 10-20 | 80-100 |
| Acidity, as HCl, Max. % | 0.001 | 0.01 | 0.05 |

In embodiments, the disclosed system and/or method are utilized to produce chlorinated paraffin wax comparable to chlorinated paraffins sold under the trade names CERECLOR S52 or CERECLOR S45. Such products may have one or more property comparable to those listed in Table 5 and may be suitable for PVC applications. The chlorinated paraffin product(s) may be suitable for use as sole plasticizers in relatively hard products (e.g. flooring compounds) or may be employed as partial replacements for phthalate or phosphate primary plasticizers. Incorporation of the treated products into PVC compositions may enhance the flame retardant properties of the final vinyl composition and provide significant cost savings in the production thereof. Due to the lower plasticizing efficiency of chlorinated paraffins and the higher density thereof, phthalates will generally not be replaced part for part by the chlorinated paraffins. Indeed, 1-5 phr (parts per hundred of rubber) of chlorinated paraffin may be included for each part of octyl phthalate replaced in various PVC compositions comprising the treated product produced herein. The incorporation of chlorinated paraffins into PVC compounds may substantially improve the resistance to cold of flexible PVC. At the temperature of injection molding, incorporation of chlorinated paraffin into PVC may reduce the viscosity of the PVC composition such that the processing rate may be increased. The flame resistance of synthetic rubber, glass fiber reinforced polyesters, polystyrene, phenolic and urea molding powders may be improved by the incorporation of chlorinated paraffins produced according to this disclosure. In such embodiments, the chlorine content of the chlorinated paraffin may be about 70 wt %.

Compositions comprising chlorinated paraffins of this disclosure, polyurethanes, polyolefins, or the like and optionally antimony trioxide may provide flame-resistant plastics. In embodiments, chlorinated paraffins of this disclosure are combined with lead fluoride and antimony oxide as additives in PVC compounds, enhancing flame resistance, waterproofing and radioactive resistance of the resulting PVC. Chlorinated paraffins of this disclosure may also be suitable for increasing the bond strength after vulcanization between nitrile rubber and neoprene or natural rubber and ethylene-propylene copolymer elastomers.

TABLE 5

Properties of Chlorinated Paraffin Wax for Use as PVC Plasticizers

| Chlorine Content, wt % | 42-45 | 50-52 | 41-44 |
| --- | --- | --- | --- |
| Average Chain Length | C15 | C15 | C21 |
| Density, g/cm³ at 25° C. | ~1.15-1.17 | ~1.23-1.26 | ~1.15-1.18 |
| Viscosity at 25° C., Pa s | 0.15-0.25 | 0.9-2 | 1.5-3 |
| Volatility, % wgt. loss on heating 180° C. for 4 h | 2.8 | 1.4 | 0.4 |
| Thermal Stability, % HCl after 4 h at 175° C. | 0.06-0.1 | 0.07-0.12 | ~0.15 |
| Toxicity | Very Low | Very Low | — |

The chlorinated paraffins of this disclosure may be utilized as paint additives. Generally, when used as paint additives, the chlorinated paraffin has a chlorine content in the range of from about 42 wt % to about 70 wt % chlorine. Such incorporation of chlorinated paraffin into paint may increase the resistance of the paint coat to chemicals, flame, and/or water. Such paints may be particularly desirable for use on objects exposed to extreme weather conditions. Lower chlorine content chloroparaffins produced via this disclosure may be suitable for use as binders and plasticizers. In embodiments, a binder comprising up to about 70 wt % chlorine is produced with a chloroparaffin produced via the system and/or method of this disclosure. Suitable chloroparaffins for use in the paint industry may have one or more of the properties presented in Table 6.

TABLE 6

Properties of Chlorinated Paraffin Wax for Use in Paint

| Chlorine Content, wt % | ~42 | ~70 | ~65 | ~70 |
| --- | --- | --- | --- | --- |
| Molecular Weight, Avg. | 570 | 1010 | 460 | 530 |
| Density, 25° C. | ~1.16 | ~1.63 | ~1.45 | ~1.55 |
| Viscosity at 25° C., Pa s | ~2.5 | — | ~35 | ~2000 |
| Color, Hazen Units | 250 | 100* | 250 | 500 |
| Thermal Stability, g HCl/100 g | ~0.15 | ~0.2 | ~0.2 | ~0.2 |

*10 parts by wt/100 parts by wt toluene

The chlorinated paraffins of this disclosure may be utilized to increase the pressure uptake capacity of gear oils and/pr hypoid oils. The use of the herein disclosed chloroparaffins in cutting oils and boring oils may substantially lengthen the service life of machine tools operated therewith. In embodiments, a fuel oil is produced by combining a few tenths of 1% of chlorinated paraffin produced via this disclosure to a conventional fuel oil. In embodiments, the setting point of the fuel oil is reduced by 10-15° C. by the addition of chlorinated paraffin thereto.

In embodiments, chlorinated paraffins of this disclosure are utilized in place of more costly or rare materials in the paint, textile, or leather industries. In embodiments, chloroparaffin (e.g. comprising ~40 wt % chlorine) is blended with polyvinylether (~25 wt %) to provide a workable substitute for fish tallow, seal oil, whale oil, or tallow.

Chlorinated paraffin produced via this disclosure may be suitable for use in the textile industry as willowing oil, carding oil, shredding oil and grease. Compositions comprising about 40 wt % chlorine may be desirable for such applications. Chlorinated paraffins produced according to this disclosure may also be suitable for use as linseed oil varnish, with the advantage that the viscosity may be altered as desired by adjusting the chlorine content of the chlorinated paraffin.

Chlorinated paraffins of this disclosure may be utilized in the food industry, for example, in packaging materials or nutrition-preserving emulsions. In embodiments, the chlorinated paraffins of this disclosure are suitable for use in the impregnation of textiles, wood, paper and other materials for reduction in flammability thereof. In embodiments, the chlorinated paraffins of this disclosure are suitable for use in the manufacture of disinfectants, dielectrics or printing inks.

Halogenation and/or sulfonation reactions will occur whenever suitable time temperature and pressure conditions exist. In embodiments, reaction occurs primarily at points outside reactor/RTV 10. In this sense halogenation and/or sulfonation can take place at any point in the flow diagram of FIG. 1 where temperature and pressure conditions are suitable for the reaction(s). Nonetheless a discrete residence time vessel 10 is often desirable to allow for increased residence time, agitation and/or cooling.

In embodiments, use of the disclosed process comprising reactant mixing via high shear device 40 allows more efficient halogenation and/or sulfonation of paraffins than conventional. In embodiments, there may be several high shear devices 40 used in series. In embodiments, the method comprises incorporating high shear device 40 into an established process thereby enabling the increase in production (greater throughput) from a process operated without high shear device 40. The superior dissolution provided by the high shear mixing may allow improvements in operating conditions such as temperature, pressure, and contact time while maintaining, or increasing, reaction rate. In embodiments, the system and method of this disclosure enable design of a smaller and/or less capital intensive process than previously possible without the incorporation of external high shear mixer 40. In embodiments, the disclosed method reduces operating costs/increases production from an existing process. Alternatively, the disclosed method may reduce capital costs for the design of new processes. Potential benefits of this modified system and method for the production of halogenated, sulfonated or sulfo-halogenated paraffins include, but are not limited to, faster cycle times, increased throughput, reduced operating costs, and/or reduced capital expense due to the possibility of designing smaller reactors and/or operating at lower temperature and/or pressure. In embodiments, conversion of reagent treatment fluid (e.g. chlorine or other halogen gas or sulfuric acid) supplied to HSD 40 is substantially complete. In embodiments, the amount of unreacted halogen is reduced by at least about 10, 20, 30, 40 or 50 percent relative to systems and methods that do not utilize high shear. In embodiments, the amount of unreacted halogen gas exiting phase separator 50 via gas line 55 is less than about 20, 15, 10, 5, 4, 3, 2, 1 or is essentially zero volume percent of the gas therein.

The products of the disclosed system and method may be suitable as a secondary (or primary) plasticizer for use in the PVC compounding industry. The products may be suitable for use, for example, in the manufacture of shoe soles, suction hosepipes, tubing, cable, wires, carpets, etc. The products may be suitable for use as flame retardants in rubber compound systems. In embodiments, the products are suitable for use in the paint industry in anticorrosives and flame proof paints. In embodiments, the product is suitable for use as a fire retardant chemical additive in (i.e. industrial) lubricants, such as gear oil. The products of the disclosed system and method may be utilizable as a flexible coating, for example, in carbon paper. Monochloroparaffin produced via the disclosed system and method may be suitable for use in the alkylation of benzene, phenol and naphthalene in the manufacture of detergents, lubricant additives (e.g. detergents, dispersing agents, antifrost agents, oxidation inhibitors) and/or textile finishing agents. Chlorinated paraffins produced hereby may also be utilized as intermediates for synthetic lubricating oils or, in the presence of aluminum or zinc chloride catalysts, can be converted into lubricant-type products by dehydrochlorination. Dehydrochlorination may also be utilized to produce olefins from the halogenated paraffin produced via this disclosure. In other embodiments, a chlorinated paraffin produced via the system and/or method of this disclosure is utilized in the manufacture of pesticide(s).

In embodiments, the disclosed system and method are utilized to chlorinate a normal (i.e. a linear) paraffin and produce a chlorinated paraffin wax suitable for use in lithium batteries. In other embodiments, the disclosed system and method are utilized to sulfonate feed material comprising N-paraffin(s) via high shear. The product sulfonates may be suitable for use in a variety of products, such as detergents, antibacterial drugs, sulfa drugs, anion exchange resins (e.g. for water purification) and dyes.

In embodiments, the system and method are utilizable to provide chlorinated paraffin products suitable for various applications including creation of metal working fluids, sealants, use in leather processing, paint and coating components, carbonless copy paper, flame retardant components and/or softeners in rubbers, textiles, PVC and other polymers. The product can comprise a single haloparaffin (e.g. a single chloroparaffin) or a mixture of various haloparaffins (e.g. a mixture of bromoparaffins). Compositions comprising the halogenated and/or sulfonated paraffin(s) produced via this disclosure can further comprise solvents and/or additives in addition to the halogenated/sulfonated product(s).

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term 'optionally' with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent they provide exemplary, procedural or other details supplementary to those set forth herein.

We claim:

1. A method for halogenating, sulfonating, or sulfo-halogenating a feed comprising paraffin, the method comprising:
introducing a mixture comprising the feed and a reagent selected from the group consisting of sulfonating agents, halogenating agents, and combinations thereof, to a high shear device, and therein subjecting the mixture to a shear rate of at least 20,000 s$^{-1}$ to produce a high-shear treated product;

cooling the high shear-treated product by heat exchange with a heat transfer medium, to produce a cooled product; and separating the cooled product into an offgas and a liquid product comprising at least one selected from the group consisting of sulfonated paraffins, halogenated paraffins, sulfo-halogenated paraffins, and combinations thereof.

2. The method of claim 1 wherein the high shear device comprises at least one rotor and at least one complementarily-shaped stator, and wherein subjecting the mixture to a shear rate of at least 20,000 s$^{-1}$ further comprises operating the high shear device at a rotor tip speed of at least 5 m/s.

3. The method of claim 1 wherein cooling the high shear-treated stream further comprises holding the high shear-treated stream in a residence time vessel configured with a heat exchanger.

4. The method of claim 1 further comprising preheating the feed.

5. The method of claim 1 wherein the feed comprises linear paraffin.

6. The method of claim 5 wherein the feed comprises paraffin wax or liquid n-paraffin.

7. The method of claim 1 wherein the feed comprises at least one selected from the group consisting of paraffin oils, paraffin waxes, and polyethylene waxes.

8. The method of claim 1 wherein the halogenating agent comprises a gas selected from the group consisting of halogens.

9. The method of claim 1 wherein the reagent is selected from the group consisting of sulfuric acid and oleum.

10. The method of claim 1 further comprising recycling at least a portion of the liquid product and forming additional high shear-treated product therefrom.

11. The method of claim 10 further comprising maintaining a desired temperature of the high shear-treated stream by adjusting at least one selected from the group consisting of the amount of reagent, the portion of the liquid product recycled, the temperature of the heat transfer medium, and the flow rate of the heat transfer medium.

12. The method of claim 1 wherein the halogenation, sulfonation, or sulfo-halogenation is conducted in the presence of a catalyst.

13. The method of claim 12 wherein the catalyst is a homogeneous chlorination catalyst selected from the group consisting of iodine, phosphorus, sulfur, antimony chloride, iron chloride, zinc chloride, and combinations thereof.

14. The method of claim 1 further comprising separating from the cooled product at least one selected from the group consisting of short chain products comprising primarily C10-C13 compounds, medium chain products comprising primarily from C14-C17 compounds, and long chain length products comprising primarily from C18-C30 compounds.

15. The method of claim 4 wherein preheating the feed comprises preheating to a temperature in the range of from about 40° C. to about 180° C. prior to introduction into the high shear device.

16. The method of claim 1 wherein the high shear treatment is performed at a temperature in the range of from about 60° C. to about 150° C.

17. The method of claim 1 wherein the high shear treatment is performed at a temperature of greater than 40° C.

18. The method of claim 1 wherein the reagent is gaseous, and wherein the high-shear treated product comprises gas bubbles having an average bubble diameter of less than about 1.5 μm.

19. The method of claim 18 wherein the high-shear treated product comprises gas bubbles having an average bubble diameter of less than about 1 μm.

20. The method of claim 1 further comprising introducing the offgas into a scrubber configured to scrub at least one component from the offgas.

* * * * *